(12) United States Patent
Nelson

(10) Patent No.: US 11,419,589 B1
(45) Date of Patent: Aug. 23, 2022

(54) BIOPSY INSTRUMENT WITH INK-FILLED MEMBRANE

(71) Applicant: Laura McGevna Nelson, Burlington, VT (US)

(72) Inventor: Laura McGevna Nelson, Burlington, VT (US)

(*) Notice: Subject to any disclaimer, the term of this patent is extended or adjusted under 35 U.S.C. 154(b) by 359 days.

(21) Appl. No.: 16/734,511

(22) Filed: Jan. 6, 2020

Related U.S. Application Data

(60) Provisional application No. 62/789,205, filed on Jan. 7, 2019.

(51) Int. Cl.
*A61B 10/02* (2006.01)
*A61B 90/00* (2016.01)

(52) U.S. Cl.
CPC .......... *A61B 10/0266* (2013.01); *A61B 90/39* (2016.02); *A61B 2090/395* (2016.02); *A61B 2090/3933* (2016.02)

(58) Field of Classification Search
CPC ..... A61B 90/02; A61B 90/39; A61B 2090/39; A61B 10/39; A61B 10/0233; A61B 10/0266; A61B 10/02–06; A61B 2090/3904–3995
USPC ........................................................ 600/564
See application file for complete search history.

(56) References Cited

U.S. PATENT DOCUMENTS

| 5,674,234 A | 10/1997 | Mccool et al. | |
|---|---|---|---|
| 8,858,484 B2 * | 10/2014 | Casey | B65D 83/0055 604/3 |
| 9,993,230 B2 | 6/2018 | Alllred | |
| 2010/0292714 A1 * | 11/2010 | Shah | A61B 17/06061 606/148 |
| 2014/0276196 A1 * | 9/2014 | Niederauer | A61B 5/411 600/556 |

\* cited by examiner

*Primary Examiner* — Matthew Kremer
*Assistant Examiner* — Om Patel
(74) *Attorney, Agent, or Firm* — STGIP, LLC; Shawn Gordon

(57) ABSTRACT

A device is provided for removing a portion of a patient's skin and leaving an ink mark on the patient's skin to demark the area of the patient's skin where the portion of the patient's skin was removed. The device may include a flexible razor or blade which may be attached to a grip or handle to facilitate cutting accurately. An ink-filled membrane is attached to the blade and/or another part of the device, such as a bottom surface of the blade, such that, when a cut is made, the membrane ruptures, retracts or is otherwise impacted so that the ink is extruded and stains the skin at the location where the cut is made so that the location may be easily located during a subsequent examination.

13 Claims, 7 Drawing Sheets

BIOPSY INSTRUMENT WITH INK-FILLED MEMBRANE

RELATED APPLICATION DATA

This application claims the benefit of U.S. Provisional Application No. 62/789,205, titled "Biopsy Instrument with Ink Membrane" and filed on Jan. 7, 2019, which is incorporated herein in its entirety.

FIELD OF THE INVENTION

The present invention generally relates to dermatology biopsy instruments. In particular, the present invention is directed to a dermatology biopsy instrument with an ink-filled membrane.

BACKGROUND

Dermatologists often remove tissue, such as lesions, cutaneous malignancies, moles, and the like, from the surface of a patient's skin. Doctors utilize various instruments for the removal of these portions of skin tissue, including, for example, thin flexible blades with finger grips, biopsy punches, and dermal curettes. It is often necessary, after a period of time, to examine the patient's skin at or around the area from which the removal was made. It can be, however, difficult to find the precise location on the patient's skin where the removal was made for a variety of reasons, such as the existence of wounds from previous similar removals or the presence of other kinds of wounds, sun damage, or disfigurements.
What is needed, therefore, is a skin tissue removal instrument that also deposits a temporary marker on the skin of the patient.

SUMMARY OF THE DISCLOSURE

In an embodiment, a biopsy device is provided that includes a flexible blade having a front edge, a left side edge, a right side edge, a top surface, and a bottom surface. A first finger grip is attached to the left side edge and a second finger grip is attached to the right side edge. A flexible connector is attached to the first finger grip and the second finger grip and passes over the top surface, and a membrane containing ink is attached to the bottom surface, wherein the membrane is designed such that forces encountered during a skin excision extrude the ink from the membrane.

In an embodiment, a dermatological biopsy instrument is provided that includes a handle, a blade attached to the handle, and an ink-filled membrane positioned such that a force is exerted on the membrane when an excision is made by the blade. The membrane is designed such that the force is sufficient to release the ink from the membrane during the excision.

In an embodiment, a method of staining a patient's skin at a location where an excision is made includes cutting a patient's skin with a blade to remove skin tissue, wherein the blade includes a membrane containing ink, and releasing the ink from the membrane during the cutting such that the ink stains the patient's skin where the skin tissue was removed.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DESCRIPTION OF THE DISCLOSURE

A device is provided for removing a portion of a patient's skin while depositing, during the process of cutting the skin, an ink or dye or similar marking substance (hereinafter, "ink") on the patient's skin to demark the area of the patient's skin at or near where the portion of the patient's skin was removed. The device may include a flexible razor or blade that may be attached to a grip or handle to facilitate cutting accurately. An ink-filled membrane is attached to the instrument and/or blade such that when a cut is made, the membrane ruptures or retracts and the ink stains the skin at the location where the cut is being made so that the location may be easily located later for examination in order to, e.g., assess whether further excision or other procedure is indicated.

Figure 1A:
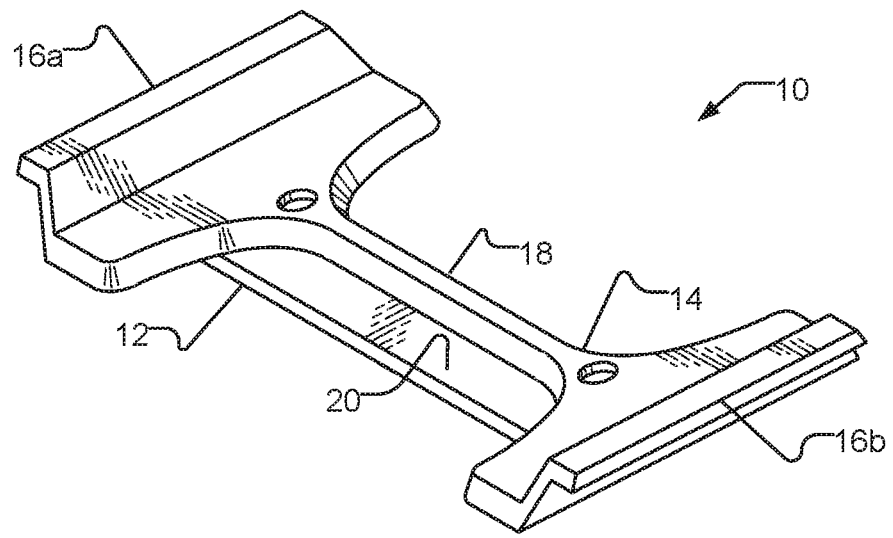
FIG. 1A is a perspective view of a prior art dermatological biopsy instrument.
Figure 1B:
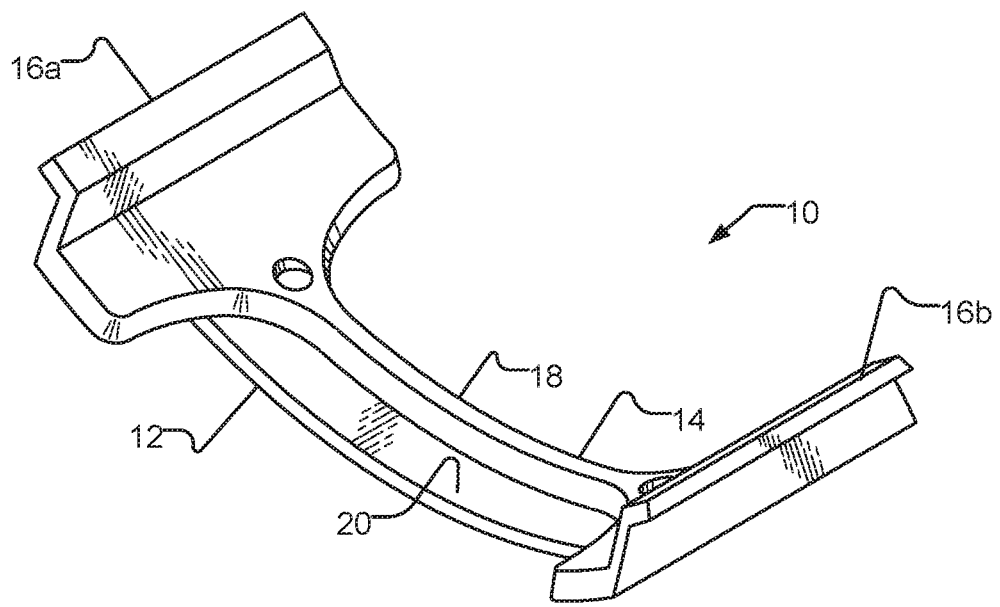
FIG. 1B is a perspective view of the prior art biopsy instrument in a flexed position.
Figure 2A:
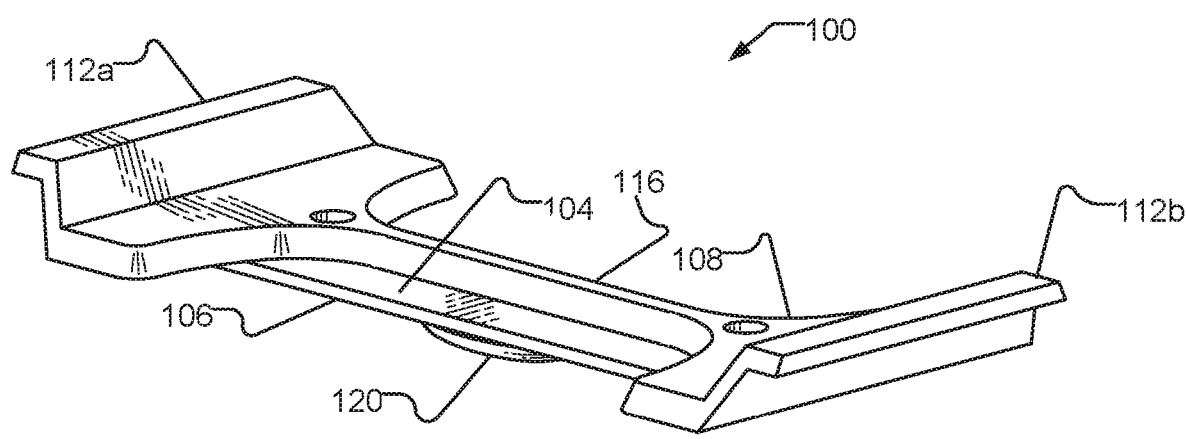
FIG. 2A is a perspective view of a dermatological biopsy instrument with an incorporated ink-filled membrane in accordance with an embodiment of the present invention.
Figure 2B:
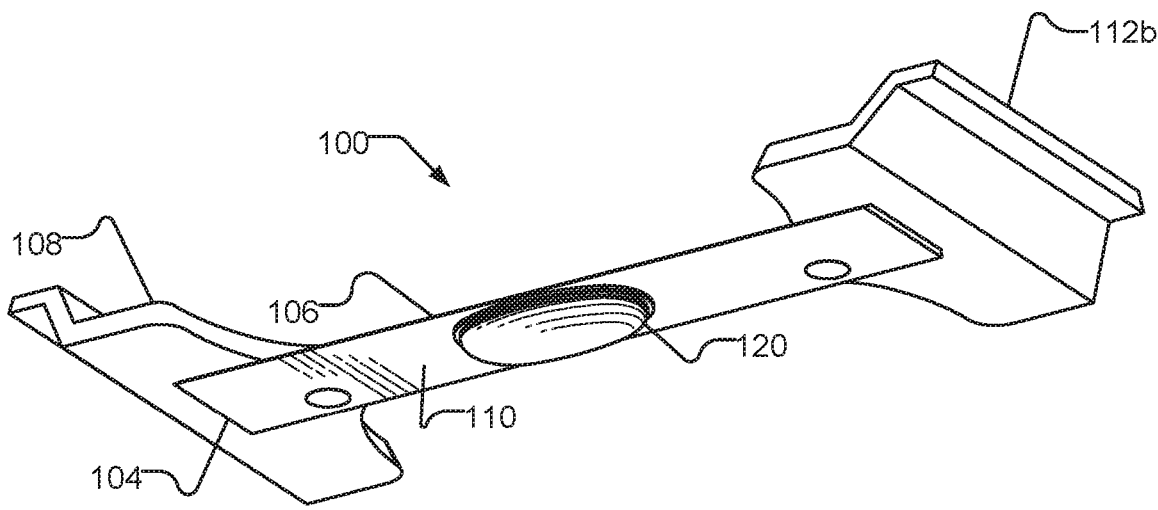
FIG. 2B is a perspective view of the dermatological biopsy instrument of FIG. 2A showing a bottom portion.
Figure 3A:
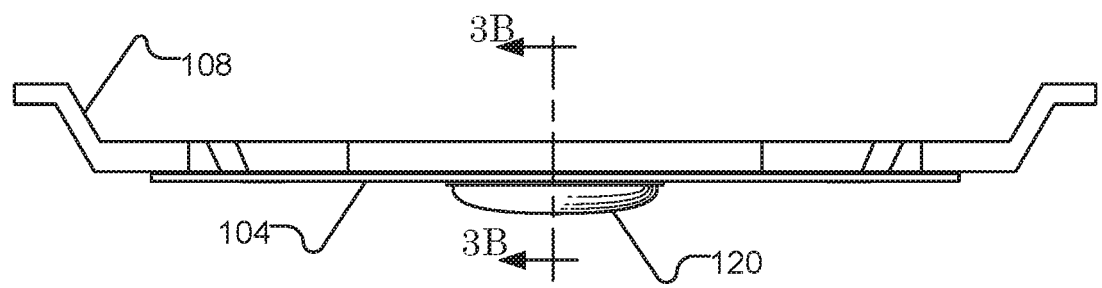
FIG. 3A is a front view of the biopsy instrument of FIG. 2A.
Figure 3B:
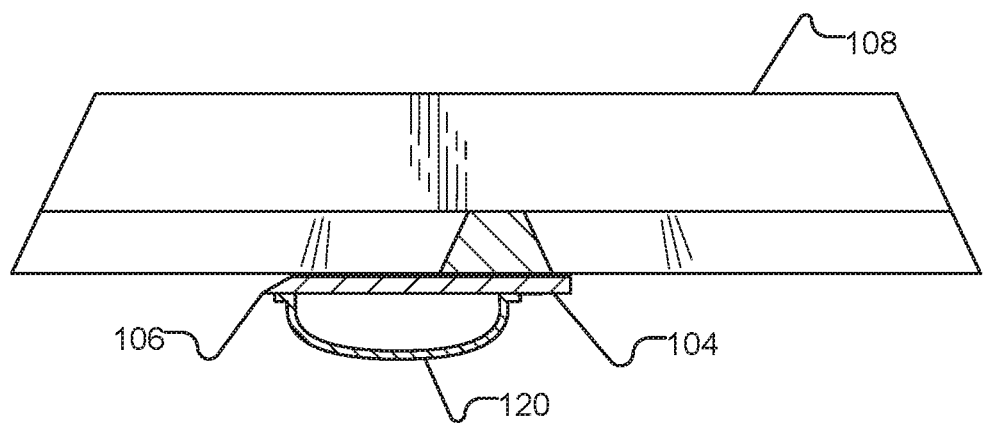
FIG. 3B. is a cross-sectional side view of the biopsy instrument of FIG. 2A.
Figure 4:
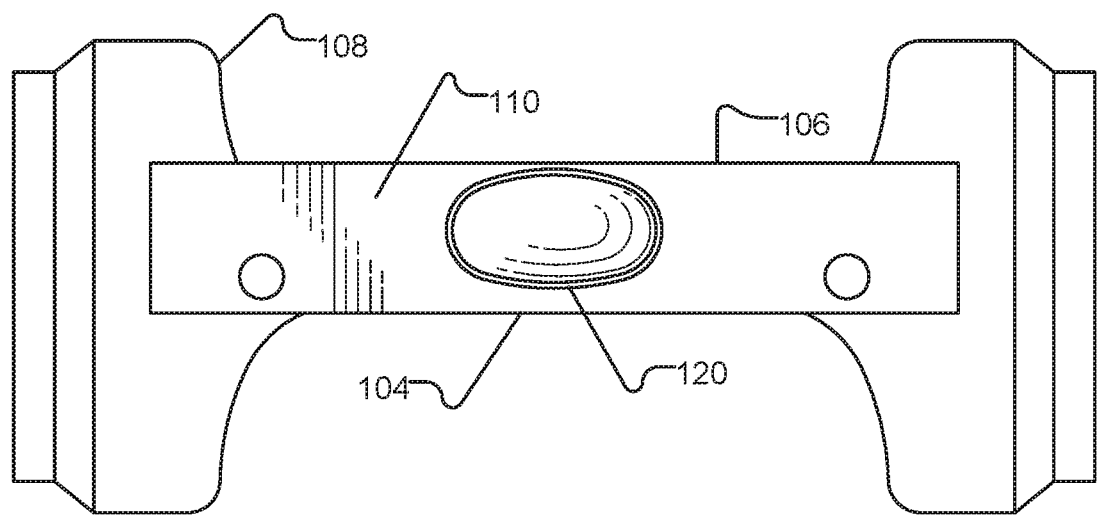
FIG. 4 is a bottom view of the biopsy instrument of FIG. 2A.
Figure 5A:
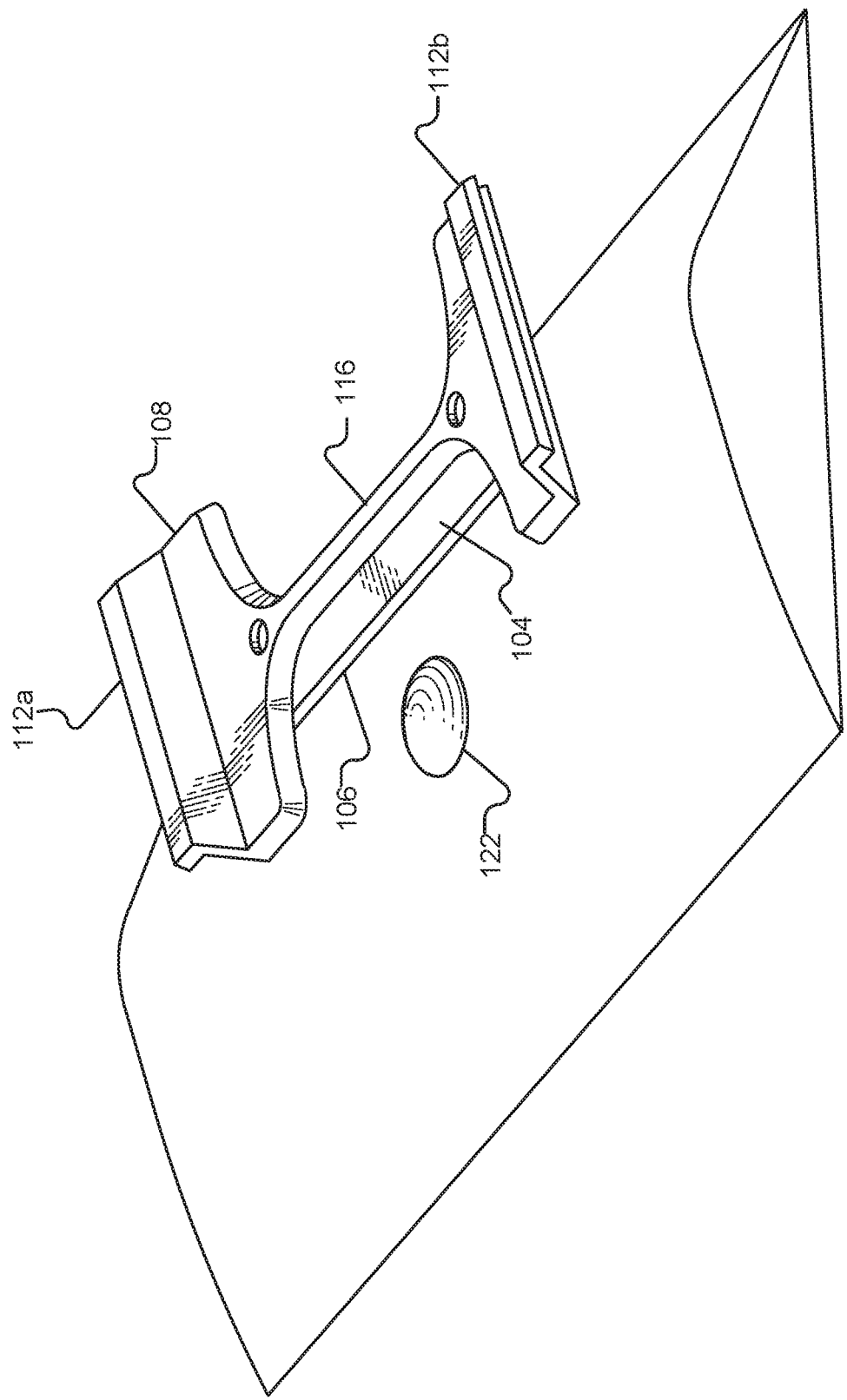
FIG. 5A is a perspective view of a biopsy instrument of an embodiment of the present invention over a practice cutting surface.
Figure 5B:
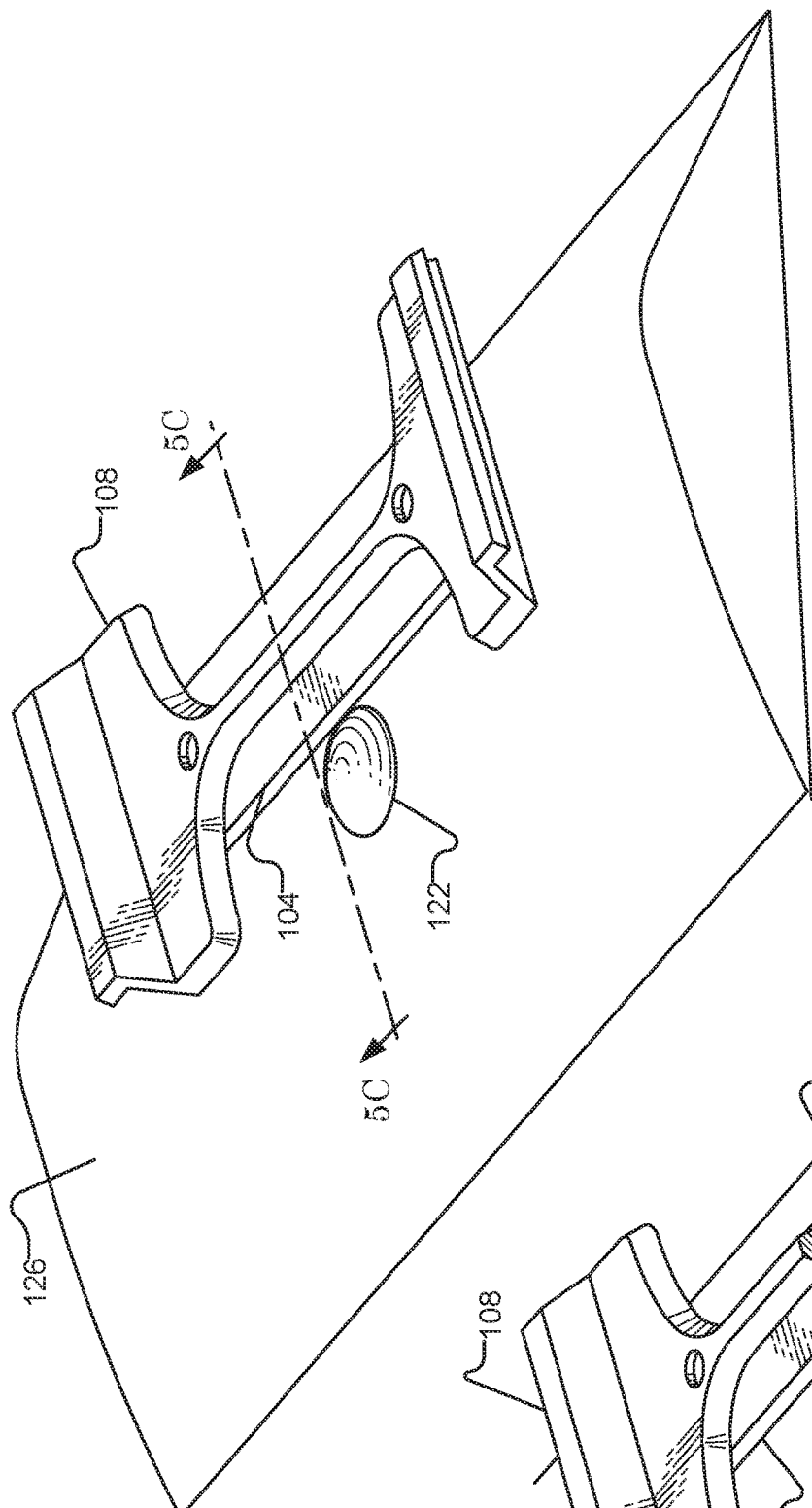
FIG. 5B shows the instrument of FIG. 5A positioned to cut a lesion.
Figure 5C:
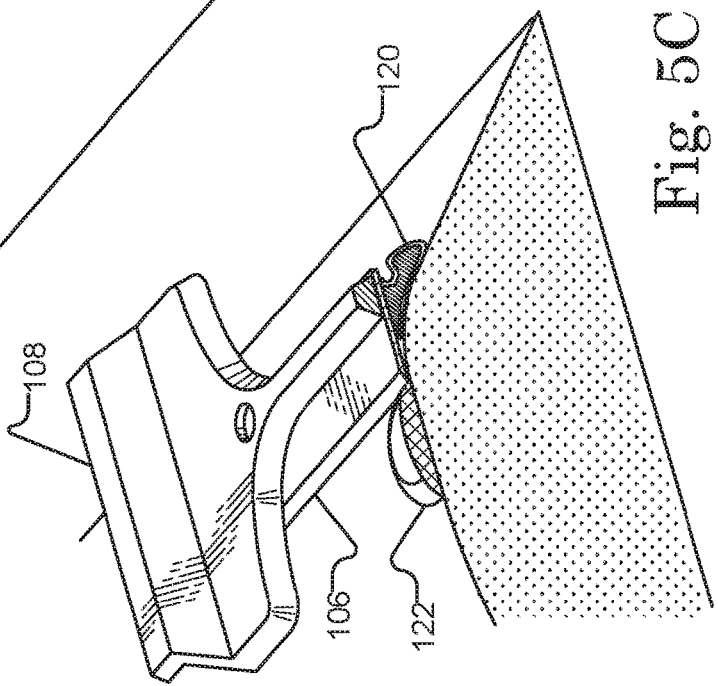
FIG. 5C is a cut-away view of FIG. 5B.
Figure 5D:
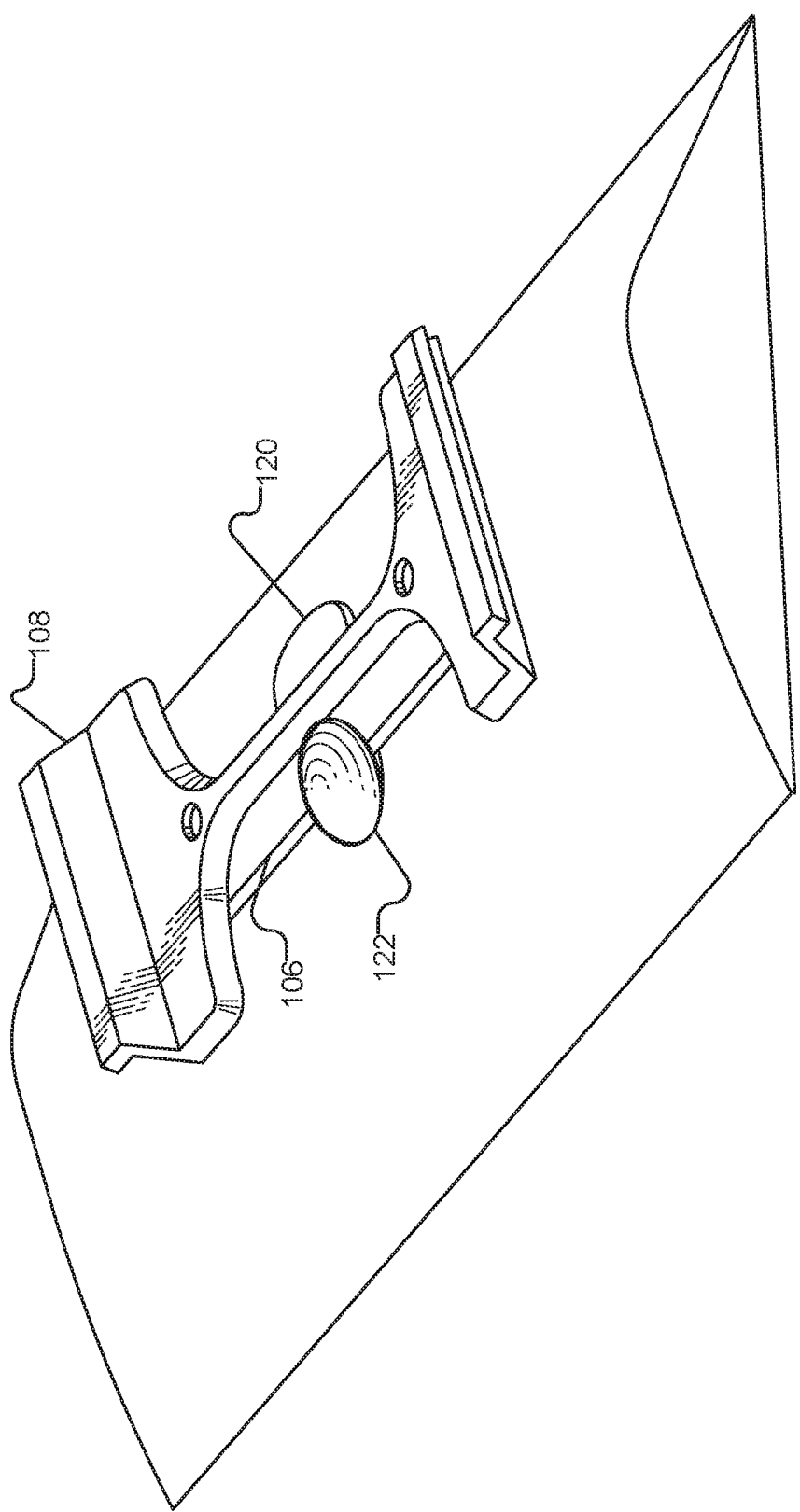
FIG. 5D depicts the instrument of FIG. 5A removing the lesion.
Figure 5E:
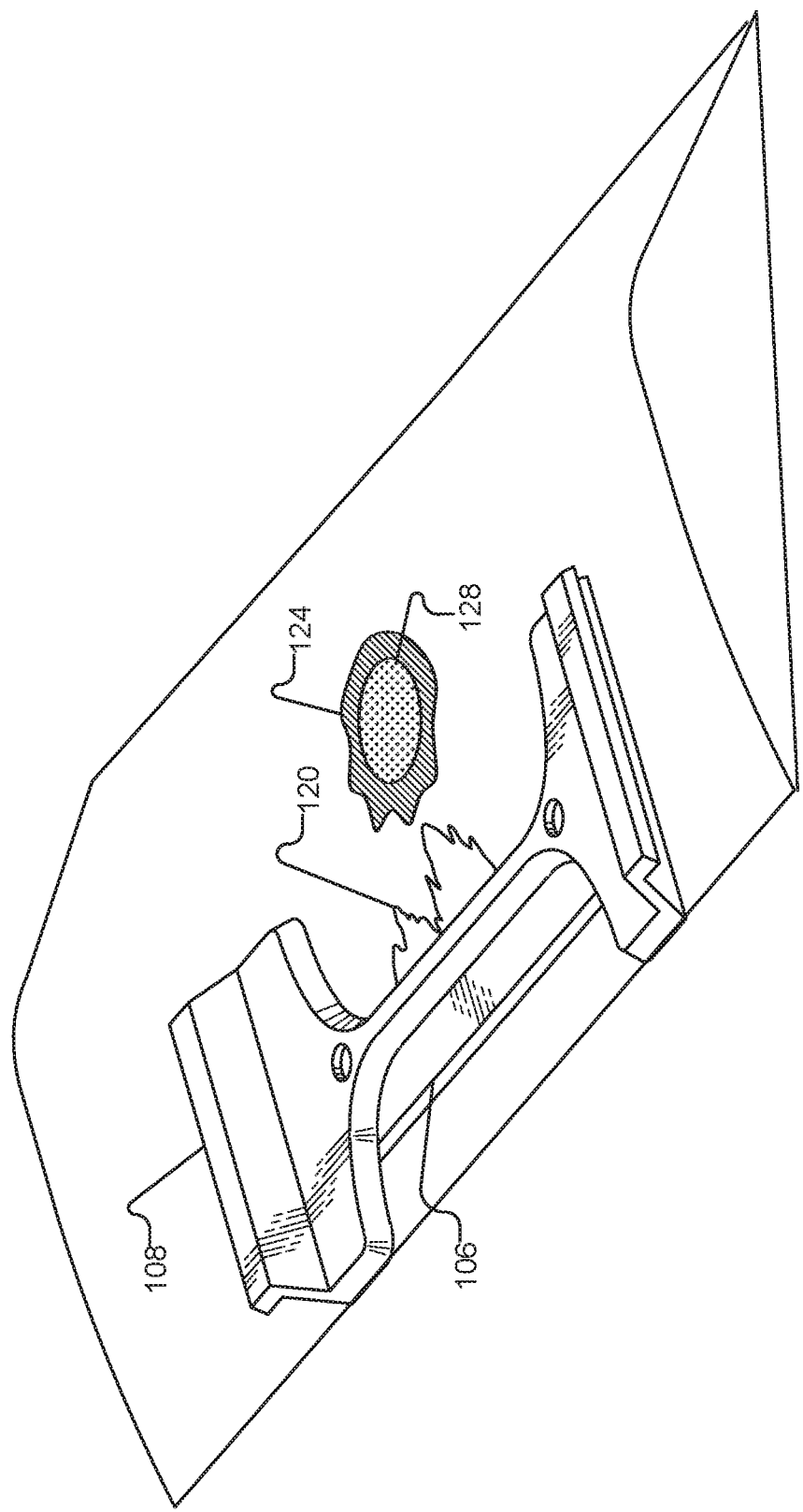
FIG. 5E depicts the instrument of FIG. 5A after a cut has been made with a ruptured or retracted membrane and an ink stain on the surface.

In FIGS. 1A-1B, a prior art biopsy instrument 10 is shown for cutting and removing portions of skin tissue, such as lesions, cutaneous malignancies, moles, and the like, at or just below the skin's surface, although it will be understood that other instruments for removing skin portions may be used in conjunction with the present invention. Biopsy instrument 10 includes a thin, flexible blade 12 attached to a handle 14 that includes a left finger grip 16a and a right finger grip 16b. A flexible sheath 18 runs above a top surface 20 of blade 12 and attaches to left finger grip 16a and right finger grip 16b. The thickness, width, and shape of the flexible sheath 18 determines in part the flexibility of biopsy instrument 10. Decreases in the thickness and/or width of the flexible sheath 18 will result in greater blade flexibility at the corresponding blade areas. The flexibility of biopsy instrument 10 allows a user to flex the instrument to an appropriate degree of curvature depending on the size and depth of the desired cut.

Turning to FIGS. 2A-4, an improved dermatological biopsy instrument 100 is shown that includes a blade 104, a handle 108 with a pair of opposing finger grips 112 (e.g., 112a, 112b), a flexible sheath 116, and a membrane 120. As shown, membrane 120 is attached to a bottom 110 of blade 104 slightly behind a front edge 106 (cutting edge) of blade 104. Preferably, membrane 120 will be approximately 1-2 mm behind front edge 106 of blade 104. Alternatively, membrane 120 may be attached in other locations and/or to handle 108 depending on the biopsy instrument being used and the type of excision to be made. Attachment may be made using any suitable technique, including for example with an adhesive, fusing, or thread.

Before a cut is made, membrane 120 contains ink and is designed to rupture, retract, invert, or open during the cutting or excision process such that ink comes out of the membrane and stains the skin where the cut is made. For example, membrane 120 may rupture during the excision due to forces encountered during the excision. Alternatively, membrane 120 may include small perforations that open to allow ink to be released under the influence of forces encountered during an excision. Membrane 120 may be made of any suitable material, including for example a thin, flexible polymer. Membrane 120 may be of any size depending on the type of excision to be made. For a typical skin biopsy, less than 1 mL of ink would be sufficient to adequately mark the skin for a later follow-up examination. The ink contained in membrane 120 may be any suitable ink that will serve to temporarily stain a patient's skin for an appropriate duration (e.g., a couple of days to up to several months).

In operation, as depicted in FIGS. 5A-5E, a biopsy instrument, such as biopsy instrument 100, is positioned at the portion of a lesion 122 on a patient's skin 126 to be removed and blade 104 is shaped in order to make a desired cut using blade 104 and/or finger grips 112a, 112b. As the cut is being made, blade 104, in combination with the patient's skin, exerts a force against membrane 120 sufficient to cause membrane 120 to rupture, retract, or otherwise be reconfigured to release ink while over the area on the skin where the cut is being made. The ink contained in membrane 120 then drains over the skin, staining the skin to leave a temporary ink stain mark 124 on, near, and/or around a location 128 on the skin where the excision was made. This allows a medical professional to easily find, during a subsequent examination, the location on the skin where the excision was made.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A biopsy device comprising:
   a flexible blade having a front cutting edge, a left side edge, a right side edge, a top surface, and a bottom surface;
   a first finger grip attached to the left side edge;
   a second finger grip attached to the right side edge;
   a flexible connector attached to the first finger grip and the second finger grip and passing over the top surface; and
   a membrane containing ink attached to the bottom surface, wherein the membrane is designed such that forces encountered by the membrane during a skin excision when the membrane is between the blade and a patient's skin are sufficient to extrude the ink from the membrane.

2. The biopsy device according to claim 1, wherein the membrane is attached to the bottom surface between 1 mm and 2 mm from the front cutting edge.

3. The biopsy device according to claim 1, wherein the membrane contains less than 1 ml of the ink.

4. The biopsy device according to claim 1, wherein the membrane is designed and configured to rupture when engaged by the forces encountered during the skin excision.

5. The biopsy device according to claim 1, wherein the membrane is configured such that the forces encountered during the skin excision retract the membrane.

6. The biopsy device according to claim 1, wherein the membrane includes a plurality of perforations sized to release the ink when the membrane is subject to the forces encountered during the skin excision.

7. A dermatological biopsy instrument comprising:
   a handle;
   a blade attached to the handle; and
   an ink-filled membrane attached to a bottom surface of the blade and positioned such that a force is exerted on the membrane when an excision is being made with the blade, wherein the membrane is designed such that the force is sufficient to release the ink from the membrane during the excision when the membrane is between the blade and a patient's skin.

8. The biopsy instrument according to claim 7, wherein the membrane is attached to the bottom surface of the blade between 1 and 2 mm from a cutting edge of the blade.

9. The biopsy instrument according to claim 7, wherein the membrane contains less than 1 ml of the ink.

10. The biopsy instrument according to claim 7, wherein the membrane is designed such that the force during the excision is sufficient to ruptures the membrane.

11. The biopsy instrument according to claim 7, wherein the membrane is designed such that the forces encountered during the excision is sufficient to retracts the membrane.

12. The biopsy instrument according to claim 7, wherein the membrane includes a plurality of perforations sized to release the ink when the membrane is subject to the force.

13. A method of staining a patient's skin at a location where an excision is made comprising:
   cutting the patient's skin with a blade to remove skin tissue, wherein the blade includes an attached membrane on a bottom surface of the blade, the attached membrane containing ink, wherein the membrane is positioned between the blade and the patient's skin during the cutting; and
   releasing the ink from the membrane during the cutting such that the ink stains the patient's skin where the skin tissue was removed.

* * * * *